United States Patent [19]

Feldman et al.

[11] Patent Number: 4,595,289
[45] Date of Patent: Jun. 17, 1986

[54] INSPECTION SYSTEM UTILIZING DARK-FIELD ILLUMINATION

[75] Inventors: Martin Feldman; Lynn O. Wilson, both of New Providence, N.J.

[73] Assignee: AT&T Bell Laboratories, Murray Hill, N.J.

[21] Appl. No.: 573,816

[22] Filed: Jan. 25, 1984

[51] Int. Cl.[4] .................. G01B 11/00; G01B 11/24
[52] U.S. Cl. .................. 356/237; 250/563; 356/392; 356/446
[58] Field of Search ............ 356/230, 232, 237, 238, 356/339, 388, 390, 392, 398, 430, 431, 446; 250/562, 563, 572; 350/523

[56] References Cited

U.S. PATENT DOCUMENTS 3,186,296  6/1965  Erban .................. 356/237
3,430,055  2/1969  Metzger .................. 356/237
4,247,203  1/1981  Levy et al. .................. 356/398
4,421,410  12/1983  Karasaki .................. 356/378

Primary Examiner—John E. Kittle
Attorney, Agent, or Firm—Eugen E. Pacher

[57] ABSTRACT

Integrated-circuit wafers and the lithographic masks and reticles used in their fabrication must be inspected for defects. Conventional systems accomplish such inspection by bright-field illumination and comparison of corresponding portions of two supposedly identical patterns on the workpiece. The minimum-size defect that can be so detected is set by misalignment between the patterns. Dark-field illumination of the portions to be compared significantly enhances the detection capabilities of such an inspection system. For a given misalignment, dark-field illumination permits the detection of defects at least four times smaller than those detectable in a conventional bright-field-illuminated system.

28 Claims, 11 Drawing Figures

SPACED-APART AREAS BEING COMPARED

INSPECTION SYSTEM UTILIZING DARK-FIELD ILLUMINATION

BACKGROUND OF THE INVENTION

This invention relates to the manufacture of integrated-circuit wafers and more particularly, to a method and an apparatus for inspecting lithographic masks and reticles used in the fabrication of such wafers and/or for inspecting the wafers themselves.

Feature widths on masks and reticles used in making integrated circuits have continued to shrink. Thus, for example, masks for one-to-one scanning printers may contain features less than about two micrometers ($\mu$m) in width, reticles for one-to-one step-and-repeat cameras may contain features less than about one $\mu$m and X-ray masks may contain feature widths of only about 0.5 $\mu$m.

Ideally, workpieces such as masks, reticles and wafers should be inspected for defects down to about half the minimum feature size. In practice, though, this is often not possible. For example, one commercially available mask inspection system is capable of detecting a minimum-size defect of only about one $\mu$m, and this capability degrades to about two $\mu$m in complex areas of the mask under inspection. (Hereinafter, the term "mask" is to be construed to mean either a mask or a reticle. This invention is applicable to the inspection of either type of element. And, as will be specified later below, the invention is also applicable to the inspection of wafers. But, for illustrative purposes, the discussion both in this background section and in the detailed description below will be primarily directed to inspecting masks.)

Conventional systems accomplish mask inspection by bright-field illumination of a portion of a chip pattern on the mask. A signal derived therefrom is compared with another signal representative of a corresponding portion of another supposedly identical chip pattern. The second portion may be viewed on-line, as described in "An Automated Mask Inspection System-AMIS," by J. H. Bruning, M. Feldman, T. S. Kinsel, E. R. Sittig and R. L. Townsend, *IEEE Transactions on Electron Devices*, Vol. ED-22, No. 7, July 1975, pp. 487–495, or as embodied in the KLA-101 Automatic Photomask Inspection System made by KLA Instruments Corporation, Santa Clara, Calif. Alternatively, a comparison signal representative of the second portion may be stored. Or such a comparison signal may be derived from software (as in the KLARIS system made by KLA). In any case, differences between the two signals are detected as defects.

In practice, the minimum-size defect that can be detected by an inspection system of the aforespecified type is set by false error indications arising from misalignment between the chip patterns being compared. At a given misalignment, the minimum detectable defect is defined as the defect which produces a signal as large as the false signal arising from the misalignment.

Misalignment between the chip patterns may arise from residual alignment errors in the inspection systems, mismatched optical distortions, mask distortions, linewidth variations, etc. Although software algorithms can help to compensate for misalignment, they are limited both by data quantization errors and by the fact there may not actually be a perfect alignment condition.

Accordingly, workers in the field have directed efforts at trying to devise improved inspection systems of the type specified above. In particular, their goal was a system capable of detecting defects smaller than those detectable by known systems. It was recognized that such efforts, if successful, could contribute significantly to improving the overall process of fabricating integrated circuits.

SUMMARY OF THE INVENTION

Hence, an object of the present invention is to improve the manufacture of integrated-circuit wafers. More specifically, an object of this invention is an improved method and apparatus for inspecting masks used in the fabrication of such wafers and/or for inspecting the wafers themselves.

Briefly, these and other objects of the present invention are realized in a specific illustrative embodiment thereof in which workpiece patterns to be compared are illuminated in a dark-field mode in which incident light is directed at the surface of the workpiece at a glancing angle. In such a mode, only light scattered from the perimeter of a feature or defect is detected. But, significantly, for a given misalignment, the ratio of defect signal-to-misalignment signal for relatively small defects is found to be much greater with dark-field illumination than with conventional bright-field illumination. Hence, dark-field illumination in an inspection system provides a basis for greatly increasing the detectability of small defects.

In accordance with applicants' invention, it is advantageous in a dark-field-illuminated inspection system to also have a bright-field-illumination capability. The reasons for this will be specified later below.

Moreover, applicants have determined that, for masks most of whose features lie along preferred directions, it is advantageous to remove dark-field-illumination from bands a few degrees wide normal to these directions. The reasons for doing this will also be specified later below.

BRIEF DESCRIPTION OF THE DRAWING

A complete understanding of the present invention and of the above and other features thereof may be gained from a consideration of the following detailed description presented hereinbelow in connection with the accompanying drawing, in which.

DETAILED DESCRIPTION

The principles of the present invention are applicable both to the inspection of masks and to the inspection of wafers. For masks, conventional bright-field illumination involves propagating light substantially normal to one main surface of the mask and collecting all or virtually all of the light transmitted through the illuminated areas and exiting from the other main surface of the mask. For wafers, conventional bright-field illumination involves propagating light substantially normal to the active or feature-containing surface of the wafer and collecting all or virtually all of the light reflected from the illuminated areas of that surface.

Hereinbelow, for purposes of a specific illustrative example, emphasis will be directed to inspecting masks. But it is to be understood that the principles of applicants' invention are applicable to inspecting both masks and wafers. In the claims, therefore, the term "workpiece" is intended to be construed to encompass masks, reticles and wafers.

Figure 1:
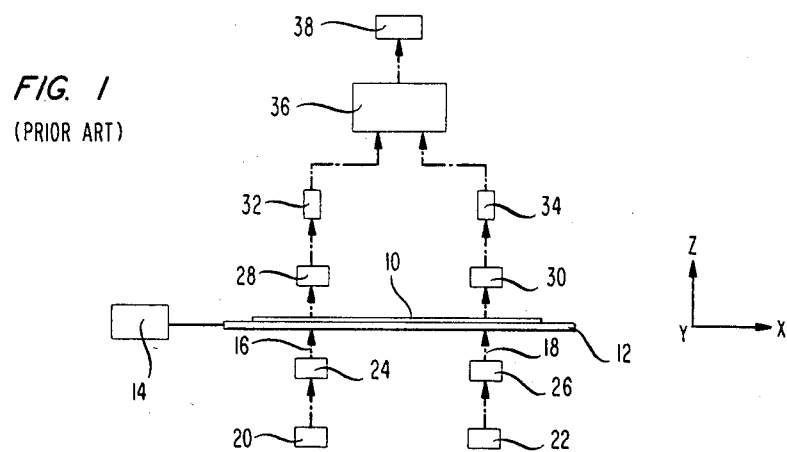
FIG. 1 depicts a known mask inspection system.

In the conventional system schematically depicted in FIG. 1, a standard workpiece 10 to be inspected is shown supported on a table 12. The table is mechanically coupled to an XY drive assembly 14.

For illustrative purposes, the workpiece 10 of FIG. 1 is assumed to be a mask. The mask 10 comprises an optically transparent substrate having thereon optically opaque features. One standard example of such a mask comprises a glass substrate with chromium features. These features define at least two supposedly identical chip patterns on the mask.

The table 12 of FIG. 1 includes an aperture centrally located below the mask 10. The dimensions of the aperture are slightly less than those of the mask. As a result, only a relatively narrow peripheral portion of the mask 10 is supported on the table 12. A main central portion of the underside of the mask 10 is thereby accessible for illumination. This main portion contains the chip features to be inspected.

In the FIG. 1 system, two spots of light are directed along dot-dash reference lines 16 and 18 at the underside of the mask 10. The spacing of the spots is selected to equal the chip spacing, or a multiple thereof, and the mask 10 is oriented so that, at any instant, the spots are directed at corresponding positions of ship patterns that were designed to be identical.

The aforespecified spots are provided by conventional sources 20, 22 and respectively associated lens assemblies 24, 26. As indicated, the incident light provided thereby is propagated along lines 16, 18 which are each perpendicular to the plane of the underside of the mask 10.

By means of the assembly 14, the table 12 of FIG. 1 is repeatedly moved in the X direction. After each X-direction scan, the table 12 is stepped a predetermined distance in the Y direction before the next X-direction scan is commenced. In that way, multiple abutting X-direction scans are carried out to inspect specified chip patterns on the mask 10.

The amount of incident light that is propagated through the mask 10 of FIG. 1 is dependent on the transmissive character of the pattern in each illuminated area. Any amount from none (area totally opaque) to all (area totally transparent) of the incident light is transmitted through the mask 10.

In the conventional so-called bright-field-illumination mode represented in FIG. 1, all or virtually all of the light transmitted through the illuminated patterned areas of the mask 10 of FIG. 1 is collected by lens assemblies 28 and 30 which comprise, for example, conventional microscope objectives. In turn, this collected light is focused onto standard photodetector arrays 32 and 34 which provide electrical output signals representative of the illuminated mask patterns.

The signals provided by the arrays 32, 34 of FIG. 1 are compared and processed in a standard signal processor and minicomputer unit 36. The unit 36 then drives a display 38 that provides, for example, a view of the chip areas being compared and a global defect map of the entire mask area.

Systems of the type briefly described above are known. The commercially available systems made by KLA are of the general type shown in FIG. 1 and described above. The system described in detail in the aforecited article by J. H. Bruning et al is also of the general type described above but includes a scanned laser source and a single photomultiplier detector per channel.

A discussion of the signals produced by circular defects and by misaligned edges in a mask inspection system will provide a basis for understanding the principles of the present invention. Such a discussion follows below in connection with FIGS. 2 and 3.

Figure 2:
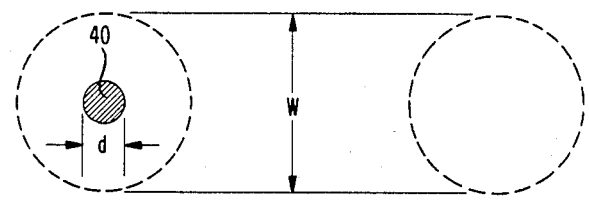
FIG. 2 represents two compared mask areas one of which contains a defect.

Assume that the viewing optics of the inspection system are characterized by a Gaussian point spread function whose full width at half maximum (FWHM) is w. (The value w also constitutes the so-called resolution element of the viewing optics.) Assume further that one of the spaced-apart chip patterns being inspected contains a centrally located opaque circular defect 40 of diameter d, as depicted in FIG. 2.

In the standard bright-field mode of mask illumination, it is apparent that the photodetector array responsive to light transmitted through the left-hand chip pattern that contains the opaque defect 40 (FIG. 2) receives less light than the other aforementioned photodetector array. As a result, a bright-field difference signal $B_{def}$ attributable to the defect 40 is generated in the unit 36 of FIG. 1. When d/w is small, $B_{def}$ can be approximated by the expression $$K_1 I_0 d^2 \qquad (1)$$

where $K_1$ is a constant and $I_0$ is the peak value of the point spread function at the photodetector array. (The constants $K_1$, $K_2$, $K_3$ and $K_4$ employed herein are roughly of the same order of magnitude.)

As mentioned earlier above, difference signals are generated in the mask inspection systems described herein even in the absence of defects. Thus, for example, relative misalignment between features in the patterns being compared also produces a difference signal. In practice, such misalignment-caused signals set the value of the minimum-size defect that can be detected by the inspection system.

Figure 3:
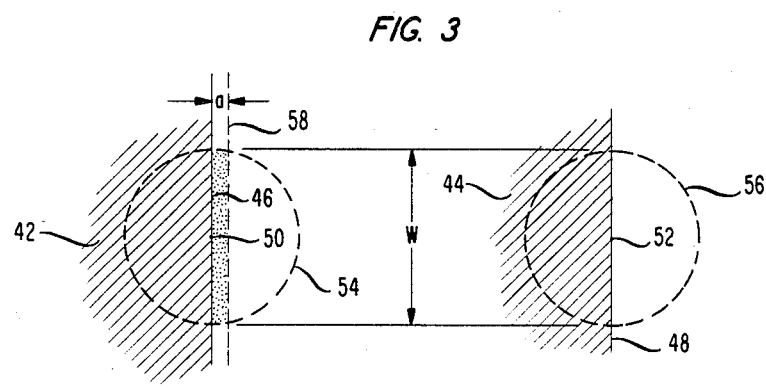
FIG. 3 represents features in two compared mask areas and illustrates a misalignment therebetween.

FIG. 3 represents portions of two feature edges included in spaced-apart chip patterns being compared in a mask inspection system of the type described herein. In an ideal system with perfect alignment, the edges of the two viewed features fall at identical corresponding points. Thus, for example, the right-hand edge of each ideal feature would extend through the center of its respective resolution element. This is schematically depicted in FIG. 3 wherein feature edges 46, 48 respectively extend through the centers 50, 52 of resolution elements 54, 56. In this ideal case, the transmitted light associated with each of the resolution elements 54, 56 would be exactly the same. Hence, no difference signal (false defect signal) would be thereby generated by the unit 36 of FIG. 1.

But, as specified earlier above, perfect alignment is rarely, if ever, achieved in practice. Thus, even in the absence of an actual defect such as an undesired opaque region on the mask, a false defect signal attributable to misalignment is typically generated during mask inspection. This is represented in FIG. 3 wherein the left-hand edge of the feature 42 is assumed, because of misalignment by a distance a relative to the aforespecified ideal condition, to fall along dashed line 58.

As a consequence of the misalignment represented in FIG. 3, it is apparent that the photodetector array responsive to bright-field light transmitted through the left-hand chip pattern receives less light than the other photodetector array shown in FIG. 1. As a result, a bright-field difference signal $B_{mis}$ attributable to the misalignment a is generated in the unit 36 of FIG. 1. When a/w is small, $B_{mis}$ can be approximated by the expression $$K_2 I_0 a w \qquad (2)$$

where $K_2$ is a constant.

Roughly speaking, when the speckled area in FIG. 3 attributable to misalignment approximately equals the area of the defect 40 of FIG. 2, the difference signal $B_{mis}$ will approximately equal the difference signal $B_{def}$. This is evident from a consideration of equations (1) and (2).

The above argument is a geometrical one based on uniform illumination of the resolution element. This gives an intuitive grasp but is not rigorously accurate. Applicants have actually considered a more detailed mathematical model which involves nonuniform (for example, Gaussian) illumination. Using that more detailed analysis for one specific illustrative bright-field system in which $w=1$ µm and $d=0.52$ µm, $B_{mis}$ approximately equals $B_{def}$ for a misalignment a of about 0.2 µm.

In accordance with one of the principles of the present invention, the chip patterns being compared in a mask inspection system are illuminated in a dark-field mode. A specific illustrative dark-field-illuminated mask inspection system is schematically depicted in FIG. 4.

For reasons that will be evident later below, the FIG. 4 system also advantageously includes a bright-field-illumination capability of the type described above in connection with FIG. 1. Thus, a number of the elements shown in FIG. 1 are also included in the FIG. 4 system which is designed to inspect the mask 10. These include the table 12, the XY assembly 14, the sources 20 and 22, the lens assemblies 24, 26, 28 ad 30, the photodetector arrays 32 and 34, the unit 36 and the display 38.

Figure 4:
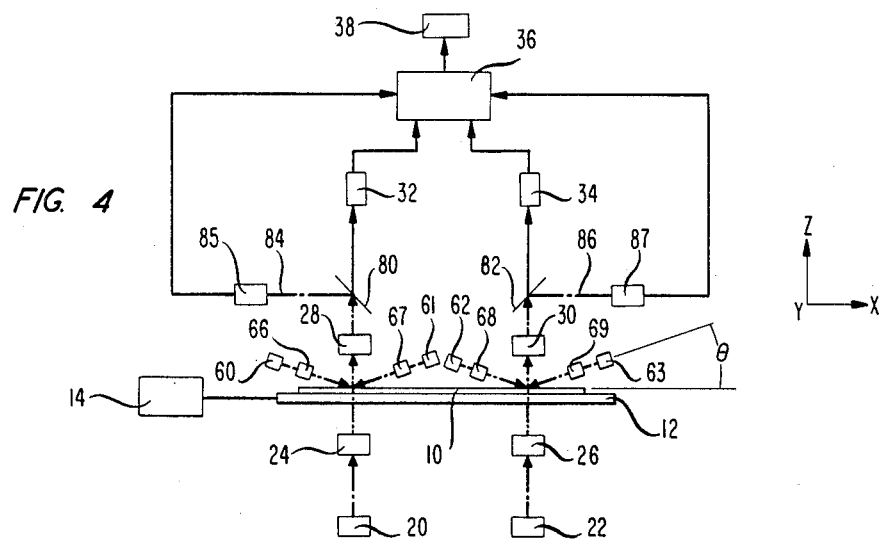
FIG. 4 is a schematic representation of a specific illustrative mask inspection system made in accordance with the principles of the present invention.

Additionally, in accordance with the principles of the present invention, the FIG. 4 system also includes sources 60 through 63 and respectively associated lens assemblies 66 through 69 which together serve to illuminate corresponding portions of two chip patterns on the mask 10 in a dark-field mode. In this mode, the mask portions are illuminated in a non-normal glancing manner. In effect, dark-field illumination outlines only the perimeter of a feature or defect on the mask.

Advantageously, for reasons that will be evident later below, the illumination provided by the sources 60 through 63 of FIG. 4 is selected to be within a specified wavelength band. This can be easily accomplished by utilizing, for example, a mercury arc lamp and an associated filter. Alternatively, each source can constitute a laser.

Advantageously, the angle $\theta$ (FIG. 4) at which light is directed at the mask 10 in the dark-field mode is selected to be in the range of 0-to-75 degrees. Illustratively, the angle $\theta$ is selected to be approximately 5 degrees.

In the dark-field mode of operation of an inspection system made in accordance with the principles of applicants' invention, only light scattered from illuminated edges of a feature or defect contained within the resolution element of the viewing optics is collected and directed to associated photodetector arrays. All other incident light is reflected and/or refracted along paths that do not fall within the entrance aperture of the collecting optics.

Figure 5:
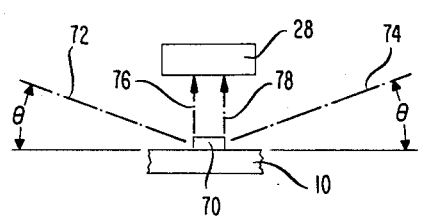
FIG. 5 shows the manner in which incident light is scattered by and collected from a feature or defect illuminated in the dark-field mode.

The aforespecified dark-field condition is illustrated in FIG. 5 wherein feature or defect 70 on one pattern on the workpiece 10 is represented as being obliquely illuminated by light beams directed thereat along center lines 72, 74. Illustratively, each beam is designed to illuminate an area approximately 300 µm in diameter on the workpiece surface.

In some cases of practical interest, dark-field illumination can be achieved by a cone of light concentric with the axis of the associated lens assembly. If, in such a case, it is desired, as discussed later below, to eliminate bands of dark-field illumination, this can easily be done by introducing stops to block selected portions of the conical illumination pattern.

Light scattered from the edges of the feature or defect 70 is represented in FIG. 5 by lines 76, 78. Only such scattered light is collected by the lens assembly 28.

Scattered light collected by the lens assemblies 28, 30 of FIG. 4 is directed at dichroic mirrors 80, 82. These mirrors are designed, for example, to reflect light directed thereat at the specified wavelength emitted by the dark-field-illumination sources 60 through 63. On the other hand, bright-field illumination provided by the sources 20, 22 at a different wavelength is designed to propagate straight through the mirrors 80, 82 to the previously mentioned photodetector arrays 32, 34. (Of course, other known techniques such as polarization separation are available for separating bright-field and dark-field illumination.)

Dark-field-derived light reflected by the mirrors 80, 82 of FIG. 4 is propagated along paths 84, 86 to respective photodetector arrays 85, 87. In turn, electrical signals generated by the arrays 85, 87 are applied to the unit 36, as indicated in FIG. 4.

In the unique dark-field mode of mask inspection described herein, it is evident that the photodetector array 85 responsive to light from the left-hand chip pattern that contains the opaque defect 40 (FIG. 2) receives more scattered light than does the photodetector array 87 which is responsive to light from the right-hand chip pattern of FIG. 2. As depicted, the right-hand chip pattern of FIG. 2 contains no edges that would scatter light toward the lens assembly 30 of FIG. 4. As a result, a dark-field difference signal $D_{def}$ attributable to the defect 40 is generated in the unit 36 of FIG. 4. When d/w is small, $D_{def}$ can be approximated by the expression $$K_3 J_0 d \qquad (3)$$

where $K_3$ is a constant and $J_0$ is the intensity per unit length of the edge source of the scattered light. For very large centrally positioned defects (d/w>>1), $D_{def}$ becomes small because the edge source falls outside the resolution element. But even then another signal will be detected when, during scanning, the viewing optics are centered over an edge of the defect.

For the particular misalignment condition represented in FIG. 3, it is seen that the length of the dark-field edge source in the left-hand chip pattern is less than that of the edge source in the right-hand chip pattern. Hence, the photodetector array 87 responsive to scattered light from the right-hand pattern receives more light than does the photodetector array 85 responsive to scattered light from the left-hand pattern. As a result, a dark-field difference signal $D_{mis}$ attributable to the misalignment a is generated in the unit 36 of FIG. 4. When a/w is small, $D_{mis}$ can be approximated (for Gaussian illumination) by the expression $$K_4 J_0 a \qquad (4)$$

where $K_4$ is a constant.

Significantly, for a given misalignment, the ratio of defect signal-to-misalignment signal is much greater for dark-field illumination than it is for bright-field illumination. In other words, for a given misalignment, a mask inspection system embodying dark-field illumination can detect defects that are considerably smaller than those detectable in a bright-field system.

In one specific illustrative dark-field system in which w=1 μm and a=0.2 μm (the same misalignment mentioned above for bright-field illumination), $D_{def}$ approximately equals $D_{mis}$ when the diameter d of a defect has a value of only about 0.11 μm. Thus, in this particular example, the diameter of the minimum-size defect detectable in applicants' dark-field inspection mode is more than four times less than in the conventional bright-field mode. The gain in sensitivity with dark-field illumination is even greater for smaller misalignments.

Figure 6:
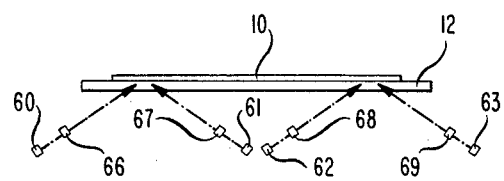
FIG. 6 shows an alternative way of providing dark-field illumination in the FIG. 4 system.

In applicants' specific illustrative inspection system shown in FIG. 4, dark-field illumination of two spaced-apart regions on the mask 10 is achieved by utilizing sources 60 through 63 that are positioned above the surface of the mask. Alternatively, dark-field illumination for mask inspection can also be effectively implemented by positioning the sources and associated lens assemblies below the mask. (For inspecting workpieces whose substrates are opaque, this alternative dark-field implementation is not feasible.) A portion of a system that embodies this alternative approach is schematically depicted in FIG. 6 wherein the sources and lens assemblies are numbered as in FIG. 4.

Figure 7:
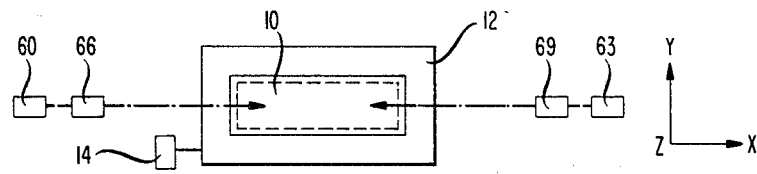
FIG. 7 is a top view of a portion of the FIG. 4 system.

FIG. 7 is a simplified top view of a portion of the FIG. 4 system. So as not to unduly clutter FIG. 7, only two of the four sources 60 through 63 utilized for dark-field illumination of the mask 10 are shown therein. These sources 60, 63 and their respectively associated lens assemblies 66, 69 are positioned to propagate light along lines that each lie in a plane perpendicular to the XY plane and wherein the line of intersection between each such pair of planes lies along or is parallel to the X axis.

Figure 8:
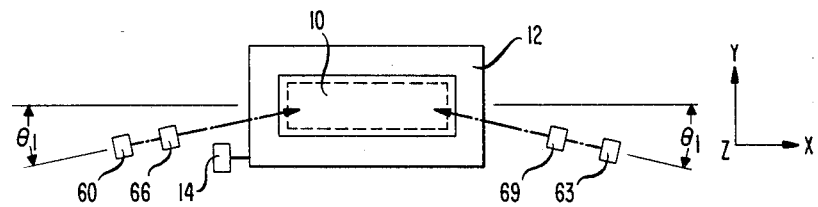
FIG. 8 is a top view of a portion of a modification of the FIG. 4 system.

In practice, the vast majority of features on most masks lie along preferred directions. In many cases, these directions constitute mutually orthogonal directions such as the X and Y directions shown in FIG. 7. In view of this, applicants recognized that it is sometimes advantageous to remove dark-field illumination from bands a few degrees wide normal to these directions. This is illustrated, for the mutually orthogonal X- and Y-direction case, in FIG. 8 wherein θ is, for example, selected to be in the range of 1-to-20 degrees. Such removal suppresses in effect much of the scattered light that would otherwise emanate from these orthogonally disposed regular features. As a result, the task of processing data in the inspection system is considerably simplified. In practice, the detection sensitivity of the system is also thereby improved.

Although dark-field illumination greatly increases the detectability of small defects, it is generally advantageous to retain some bright-field capability even at a reduced sensitivity. There are several reasons for doing so. First, the tone of large defects can thereby be determined. Second, large defects will not be missed. And, third, opaque particles within large opaque areas can be thereby identified and disregarded if desired.

Accordingly, the specific illustrative inspection system shown in FIG. 4 includes both dark-field and bright-field illumination capabilities. By utilizing one or the other, or both types of illumination simultaneously, an advantageous system is achieved. Such a system represents a significant improvement in the field of mask inspection.

Figure 11:
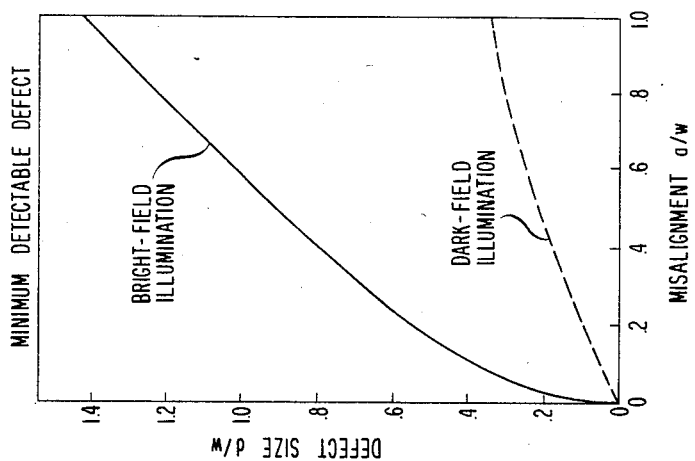
FIGS. 9 through 11 are graphs helpful in comparing the conventional bright-field mode with applicants' inventive dark-field mode of inspection.
Figure 10:
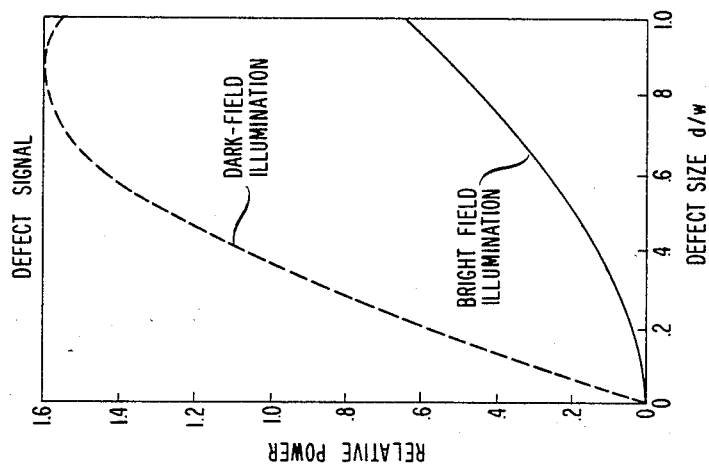
Figure 9:
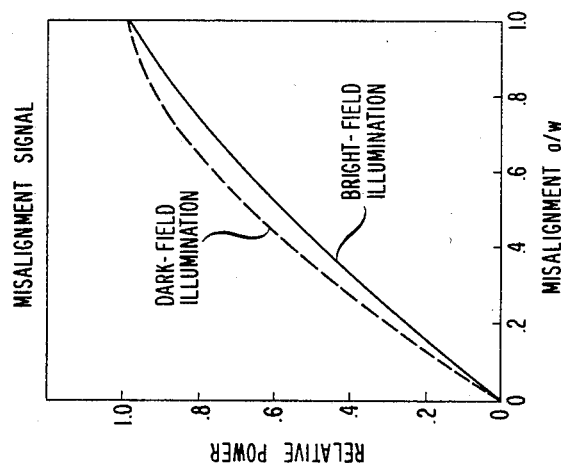

Much of the herein-described comparison of bright-field and dark-field inspection modes is graphically depicted in FIGS. 9 through 11 which represent the results of a mathematical analysis for Gaussian illumination. In FIG. 9, relative bright-field and dark-field signal levels due to misalignment are shown as a function of the normalized misalignment a/w. The horizontal scale is normalized with respect to the FWHM w of the point spread function. Thus, for example, if the resolution of the viewing optics is one μm FWHM, the horizontal scale reads directly in microns. Illustratively, this resolution is readily obtained with blue light and a lens assembly having a numerical aperture of about 0.2. The normalization of the signals has been chosen so that at a/w=1, the dark- and bright-field misalignment signals are equal. As indicated in FIG. 9, the two signals are approximately equal to each other over the entire range of a/w.

In FIG. 10, the bright- and dark-field signals due to a circular defect are shown, using the same normalizations and vertical scale as in FIG. 9. It is evident, therefore, that for a given misalignment and defect size, the ratio of defect signal-to-misalignment signal is much greater for dark-field illumination than for bright-field illumination.

FIG. 11 shows the threshold for detecting defects without having false error indications due to misalignments. FIG. 11 is a plot of the size d of a defect that gives the same signal as a misalignment of size a: $B_{def}(d) = B_{mis}(a)$ and $D_{def}(d) = D_{mis}(a)$. FIG. 11 shows that with dark-field illumination the threshold for detecting defects without false error indications is at least a factor of four smaller than with bright-field illumination.

Finally, it is to be understood that the above-described inspection techniques are only illustrative of the principles of the present invention. In accordance with these principles, numerous modifications and alternatives may be derived by those skilled in the art without departing from the spirit and scope of the invention.

What is claimed is:

1. Apparatus for inspecting corresponding portions of patterns that comprise features defined on a substrate and for providing an indication of defects in said portions, said apparatus comprising means for illuminating said corresponding portions in a dark-field mode to scatter light from illuminated feature or defect edges, and means responsive only to light scattered from edges in said corresponding portions for generating difference signals representative of defects in said illuminated portions.

2. Apparatus as in claim 1 further including means for illuminating said corresponding portions in a bright-field mode, and means responsive only to bright-field-mode light from said corresponding portions for generating difference signals representative of defects in said illuminated portions.

3. Apparatus as in claim 2 wherein said responsive means includes means for distinguishing between dark-field-mode light scattered from edges in said corresponding portions and bright-field-mode light from said corresponding portions.

4. Apparatus as in claim 3 wherein said dark-field illuminating means comprises means for directing light at said corresponding portions along center lines that each form an angle in the range of 0-to-75 degrees with the plane of said substrate.

5. Apparatus as in claim 4 wherein said patterned substrate is mounted on a table and said apparatus further comprises means for moving said table successively in orthogonal directions to accomplish scanning of the patterns to be inspected.

6. Apparatus as in claim 5 wherein the dark-field illuminating means are positioned above the top surface of the substrate mounted on said table.

7. Apparatus as in claim 5 wherein the dark-field illuminating means are positioned below said table.

8. Apparatus as in claim 6 wherein most of the feature edges in said patterns lie along or parallel to orthogonally disposed axes, and wherein the directions of incident dark-field illumination are selected to minimize collectible light scattered from said feature edges.

9. Apparatus as in claim 7 wherein most of the feature edges in said patterns lie along or parallel to orthogonally disposed axes, and wherein the directions of incident dark-field illumination are selected to minimize collectible light scattered from said feature edges.

10. Defect-detecting apparatus for inspecting a workpiece that includes features on a substrate, the features constituting at least two patterns that are intended to be identical, said apparatus comprising two photodetector arrays, two lens assemblies respectively associated with said arrays, each assembly being responsive to incident scattered light from a respective corresponding pattern portion for directing said light onto its respective array, means for illuminating corresponding portions of said patterns only at a glancing angle in a dark-field mode to cause light to be scattered from edges in said portions and towards said respective lens assemblies, and means responsive to electrical signals provided by said photodetector arrays for in effect comparing the light scattered from said illuminated portions and thereby providing an indication of defects in said portions.

11. Apparatus as in claim 10 also including means for illuminating corresponding portions of said patterns in a bright-field mode.

12. Apparatus as in claim 11 further including two additional photodetector arrays responsive to bright-field light directed thereat by said respective lens assemblies.

13. Apparatus as in claim 12 further including means interposed between each lens assembly and its respective associated pair of photodetector arrays for directing dark-field scattered light onto one array of the pair and for directing bright-field light onto the other array of the pair.

14. Apparatus as in claim 13 wherein said directing means interposed between each lens assembly and its respective associated pair of photodetector arrays comprises a dichroic mirror.

15. A method of inspecting a workpiece for defects, the workpiece comprising a substrate having features thereon, the features constituting at least two supposedly identical patterns, said method comprising the steps of illuminating corresponding portions of said patterns in a dark-field mode to cause light to be scattered from edges of features and defects included in said portions, collecting substantially only said scattered light, and utilizing only said collected light to generate output signals representative of the defect condition of said illuminated portions.

16. A method as in claim 15 wherein the edges of a substantial number of the features on said workpiece lie along or parallel to preferred axes, and wherein the directions of incident dark-field illumination are selected to minimize collectible light scattered from said feature edges.

17. A method as in claim 15 wherein said workpiece comprises a mask including a transparent substrate having opaque features thereon.

18. A method as in claim 17 wherein said corresponding portions are also illuminated in a bright-field mode to transmit light through illuminated transparent regions of said portions.

19. A method as in claim 15 wherein said workpiece comprises a wafer.

20. A method as in claim 19 wherein said corresponding portions are also illuminated in a bright-field mode to reflect light from illuminated regions of said portions.

21. Apparatus for inspecting a workpiece to determine whether or not a region thereof is patterned in accordance with prescribed design standards, said apparatus comprising means for illuminating said region to cause light to be scattered from feature or defect edges in said region, means for collecting only light scattered from the entire extent of said edges and for providing an output signal representative thereof, means for providing a comparison signal derived from a pattern supposedly identical to the one in said region, and means for comparing said signals to provide an indication of whether or not said region is patterned in accordance with said prescribed design standards.

22. Apparatus as in claim 21 wherein said comparison signal is derived from another supposedly identically patterned region on said same workpiece.

23. Apparatus as in claim 21 wherein said comparison signal is derived from another supposedly identically patterned region on another workpiece.

24. Apparatus as in claim 21 wherein said comparison signal is derived from a stored representation of the prescribed pattern in said region.

25. A method of inspecting a workpiece to determine whether or not a region thereof is patterned in accordance with prescribed design standards, said method comprising the steps of
   illuminating said region to cause light to be scattered from feature or defect edges in said region,
   collecting only light scattered from the entire extent of said edges and for providing an output signal representative thereof,
   providing a comparison signal derived from a pattern supposedly identical to the one in said region,
   and comparing said signals to provide an indication of whether or not said region is patterned in accordance with said prescribed design standards.

26. A method as in claim 25 wherein said comparison signal is derived from another supposedly identically patterned region on said same workpiece.

27. A method as in claim 25 wherein said comparison signal is derived from another supposedly identically patterned region on another workpiece.

28. A method as in claim 25 wherein said comparison signal is derived from a stored representation of the prescribed pattern in said region.

* * * * *